United States Patent
Kudlik (10) Patent No.: US 11,235,139 B2
(45) Date of Patent: Feb. 1, 2022

(54) CURRENT-SPEED RELATIONSHIP FOR INSTANTANEOUS SUCTION DETECTION ALGORITHM IN LVADS

(71) Applicant: HeartWare, Inc., Miami Lakes, FL (US)

(72) Inventor: D'Anne E. Kudlik, Lino Lakes, MN (US)

(73) Assignee: HeartWare, Inc., Miami Lakes, FL (US)

( * ) Notice: Subject to any disclaimer, the term of this patent is extended or adjusted under 35 U.S.C. 154(b) by 79 days.

(21) Appl. No.: 16/406,220

(22) Filed: May 8, 2019

(65) Prior Publication Data

US 2019/0351116 A1    Nov. 21, 2019

Related U.S. Application Data

(60) Provisional application No. 62/672,668, filed on May 17, 2018.

(51) Int. Cl.
  *A61M 60/50*    (2021.01)
  *G16H 20/40*    (2018.01)

(52) U.S. Cl.
  CPC .......... *A61M 60/50* (2021.01); *G16H 20/40* (2018.01); *A61M 2205/18* (2013.01); *A61M 2205/3331* (2013.01); *A61M 2205/50* (2013.01)

(58) Field of Classification Search
  CPC .......................... A61M 60/50; A61M 1/1086
  See application file for complete search history.

(56) References Cited

U.S. PATENT DOCUMENTS

| | | |
|---|---|---|
| 6,066,086 A | 5/2000 | Antaki et al. |
| 7,997,854 B2 | 8/2011 | LaRose et al. |
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 9,511,179 B2 | 12/2016 | Casas et al. |

(Continued)

FOREIGN PATENT DOCUMENTS

WO    2015179921 A1    12/2015

OTHER PUBLICATIONS

International Search Report and Written Opinion dated Aug. 6, 2019, for corresponding International Application No. PCT/US2019/031253; International Filing Date: May 8, 2019 consisting of 11-pages.

*Primary Examiner* — Michael W Kahelin
*Assistant Examiner* — Naveed R. Kolia
(74) *Attorney, Agent, or Firm* — Shumaker & Sieffert, P.A.

(57) ABSTRACT

A system for detecting a suction condition in an implantable blood pump including a controller in communication with the blood pump. The controller includes a control circuit configured to calculate a present value during a time period, the present value corresponding to a pump speed divided by a pump current, determine a plurality of data values during the time period based on the present value, and determine a suction detection threshold value using the plurality of data values. The control circuit is also configured to compare the present value during the time period to the suction detection threshold value and generate an alert when the present value exceeds the suction detection threshold value on a plurality of instances during the time period, the alert corresponding to a suction condition.

8 Claims, 10 Drawing Sheets

(56) References Cited

U.S. PATENT DOCUMENTS

| | | | |
|---|---|---|---|
| 9,561,313 B2 | 2/2017 | Taskin | |
| 2004/0133061 A1* | 7/2004 | Nose | A61M 60/148 600/16 |
| 2010/0174231 A1* | 7/2010 | Horvath | F04D 15/0066 604/67 |
| 2015/0322940 A1* | 11/2015 | Horvath | F04D 15/0066 417/42 |
| 2015/0367048 A1* | 12/2015 | Brown | A61M 60/40 600/17 |
| 2018/0085507 A1 | 3/2018 | Casas et al. | |

* cited by examiner

CURRENT-SPEED RELATIONSHIP FOR INSTANTANEOUS SUCTION DETECTION ALGORITHM IN LVADS

CROSS-REFERENCE TO RELATED APPLICATION

This application claims the benefit of U.S. Application Ser. No. 62/672,668, filed May 17, 2018.

FIELD

The present technology is generally related to a system and method for detecting an adverse event, such as a suction condition, within an implantable blood pump.

BACKGROUND

Implantable blood pumps are commonly used to assist the pumping action of a failing heart. Typically, blood pumps include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A blood pump may be configured as a ventricular assist device ("VAD"). Exemplary VADs include the HVAD® pump and the MVAD® pump manufactured by HeartWare, Inc. in Miami Lakes, Fla., USA. The HVAD® pump is further discussed in U.S. Pat. No. 8,512,013 and the MVAD® pump is further discussed in U.S. Pat. Nos. 8,007,254 and 9,561,313, the disclosures of which are incorporated herein in the entirety.

To provide clinically useful assistance to the heart, VADs impel blood at a relatively substantial rate. However, when the VAD is operated at a flow rate in excess of the inflow rate of blood to the ventricle, the VAD will create a suction condition within the ventricle and the ventricle may collapse from the blood deficiency. A suction condition may also be produced when the intake or outlet of the VAD is obstructed. The suction condition causes a decline in flow rate which creates a vacuum, thereby causing the pump speed to significantly increase relative to a normal operative speed. In response thereto, the current may be reduced in an effort to return the pump speed to the normal operative speed. Unfortunately, known systems and methods may detect the suction condition using a flow waveform, which delays the time of detection, thereby increasing the risk of harm to the patient.

SUMMARY

The techniques of this disclosure generally relate to a system and method for detecting an adverse event, such as a suction condition, within an implantable blood pump.

In one aspect, the present disclosure provides a system for detecting a suction condition in an implantable blood pump including a controller in communication with the blood pump, the controller including a control circuit configured to: calculate a plurality of data values using a hysteresis window, calculate a present value during a time period, the present value corresponding to a pump speed divided by a pump current following the hysteresis window, determine a suction detection threshold value using the plurality of data values, compare the present value during the time period to the suction detection threshold value, and generate an alert when the present value exceeds the suction detection threshold value on a plurality of consecutive instances during the time period, the alert corresponding to a suction condition.

In another aspect, the time period is a one to five second hysteresis window.

In another aspect, the plurality of data values includes a baseline value waveform between a 50th to 75th percentile relative to the hysteresis window.

In another aspect, the baseline value waveform is an adaptive value.

In another aspect, the plurality of data values includes a first pulsatility percentile value between a 5th to 30th percentile relative to the hysteresis window and a second pulsatility percentile value between a 70th to 95th percentile value relative to the hysteresis window.

In another aspect, the control circuit is configured to calculate a pulsatility value waveform corresponding to a difference between the first pulsatility percentile value and the second pulsatility percentile value.

In another aspect, the control circuit is configured to determine the suction detection threshold value using a suction detection equation, the suction detection equation including adding the baseline value waveform to the pulsatility value waveform, the pulsatility value waveform being multiplied by a multiplier.

In another aspect, the multiplier is a constant over a plurality of time periods.

In another aspect, the control circuit is configured to classify a severity of the suction condition.

In one aspect, a method for detecting a suction condition in an implantable blood pump includes calculating a plurality of data values using a hysteresis window. A present value during a time period following the hysteresis window is calculated, the present value corresponding to a pump speed divided by a pump current. A suction detection threshold value is determined using the plurality of data values. The present value during the time period is compared to the suction detection threshold value. An alert is generated when the present value exceeds the suction detection threshold value on at least one instance during the time period, the alert corresponding to a suction condition.

In another aspect, the time period is a one to five second hysteresis window.

In another aspect, the method further includes determining a baseline value waveform between a 50th to 75th percentile relative to the hysteresis window.

In another aspect, the method further includes determining a pulsatility value waveform corresponding to a difference between a first pulsatility percentile value and a second pulsatility percentile value relative to the hysteresis window.

In another aspect, the method further includes executing a suction detection equation, the suction detection equation including adding the baseline value waveform to the pulsatility value waveform, the pulsatility value waveform being multiplied by a multiplier.

In another aspect, the multiplier is a constant over a plurality of time periods.

In another aspect, the method further includes classifying a severity of the suction condition.

In another aspect, the method further includes instantaneously determining the suction condition at an onset thereof.

In another aspect, the method further includes sending the alert to a location remote from a location of the blood pump.

In another aspect, the method further includes recording the plurality of instances when the present value exceeds the suction detection threshold value using a present waveform.

In one aspect a method for detecting a suction condition in an implantable blood pump includes calculating a baseline value waveform and a pulsatility value waveform relative to a hysteresis window. A present value during a time period following the hysteresis window is calculated, the present value corresponding to a pump speed divided by a pump current. a suction detection threshold value is determined using the baseline value waveform and the pulsatility value waveform. An alert is generated when the present value exceeds the suction detection threshold value on at least one instance during the time period.

In one aspect, a method of detecting an adverse event in an implantable blood pump includes determining a present value at a select time. The present value at the select time minus one is determined. The determined present value at the select time is compared and the determined present value at the select time minus one is compared to a threshold. At least one pump parameter is adjusted in response to the determined present value at the select time and the determined present value at the select time minus one exceeding the threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the configurations reside primarily in combinations of system components and method steps related to detecting a suction condition within an implantable blood pump. Accordingly, the system and method components have been represented where appropriate by conventional symbols in the drawings, showing only those specific details that are pertinent to understanding the configurations of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 1:
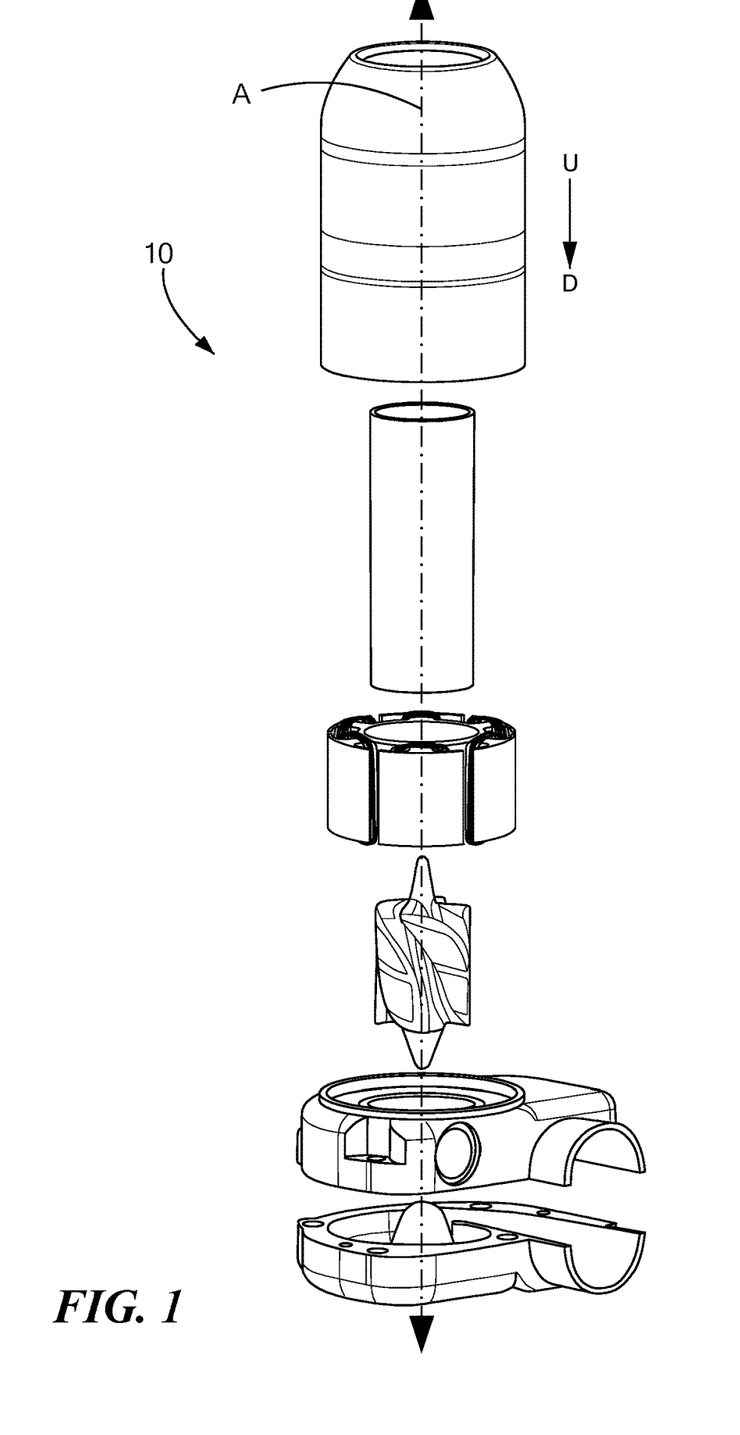
FIG. 1 is a schematic view of an exemplary blood pump.

Referring now to the drawings in which like reference designators refer to like elements there is shown in FIG. 1 an exemplary implantable blood pump 10 configured to be implanted within a patient, such as a human or animal patient. The blood pump 10 may be, without limitation, the HVAD® Pump or the MVAD® Pump, having a movable element, such as a rotor, configured to pump blood from the heart to the rest of the body. The HVAD® Pump is further discussed in commonly owned U.S. Pat. Nos. 7,997,854 and 8,512,013, and the MVAD® Pump is further discussed in commonly owned U.S. Pat. Nos. 8,007,254, 8,419,609, and 9,561,313, the disclosures of which are incorporated herein by reference in the entirety.

Figure 2:
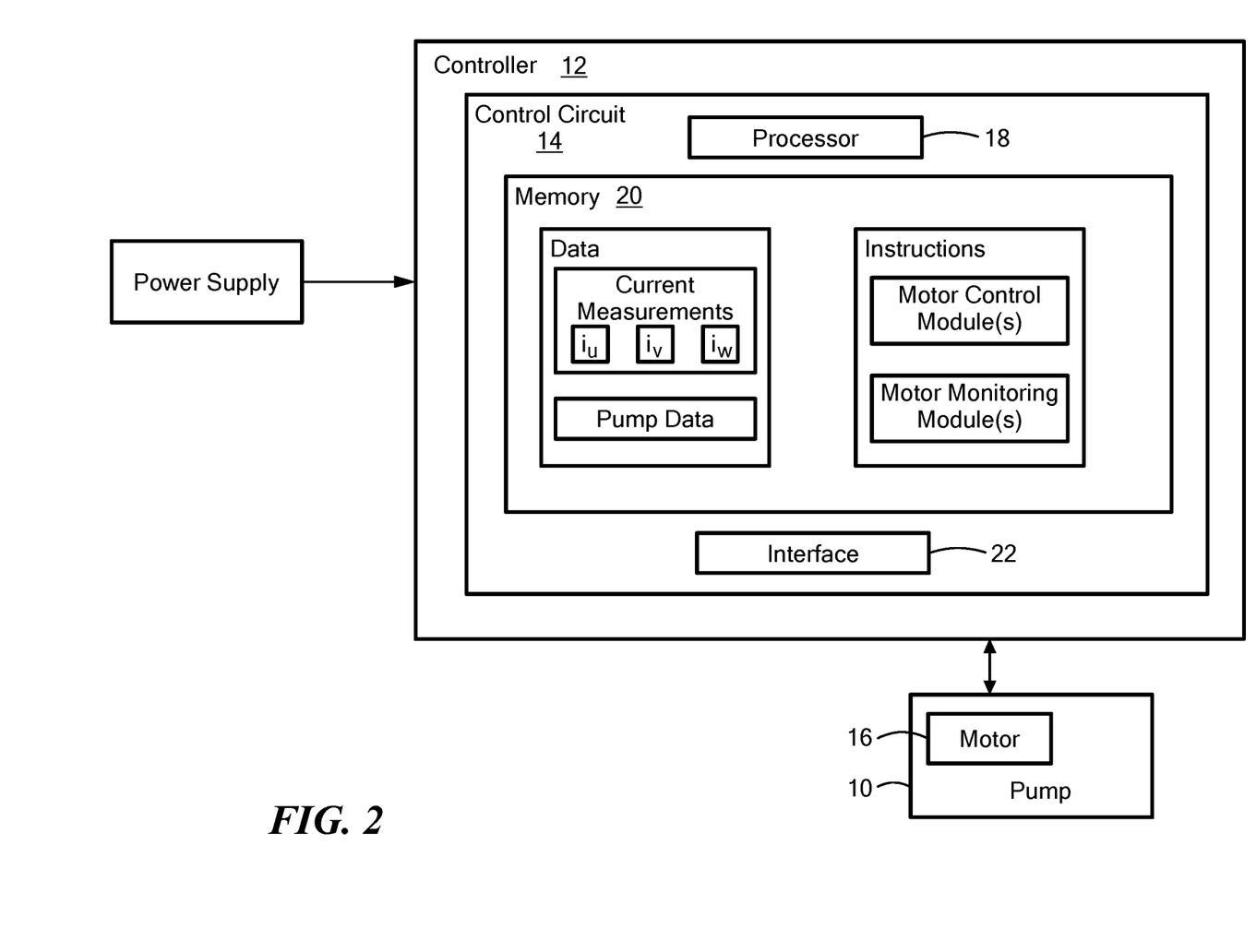
FIG. 2 is an exemplary system which may be used to perform one more of the method steps of detecting a suction condition within the blood pump of FIG. 1.

With reference to FIG. 2, an exemplary system is depicted including the blood pump 10 in communication with a controller 12 and a control circuit 14 for monitoring and controlling startup and subsequent operation of a motor 16 implanted within the blood pump 10 and performing one or more of the method steps disclosed herein. The method and system disclosed herein may be used with axial or centrifugal blood pumps.

In one configuration, the controller 12 and the control circuit 14 are configured to detect an adverse event associated with the blood pump 10, such as a suction condition present within the blood pump 10. In order to detect the suction condition, for example, the controller 12 may be configured to determine, monitor, and/or track one or more parameters associated with the blood pump 10, for example, the amount of power usage, electrical current, voltage, and/or back electromotive force ("BEMF"), as discussed in commonly owned U.S. Pat. No. 9,511,179, which is incorporated by reference herein in the entirety. As commonly understood by a person of ordinary skill in the art, BEMF is the voltage in a coil of the motor 16 that opposes current flowing through the coil when the armature rotates.

The controller 12 may also include a processor 18 in communication with the control circuit 14, a memory 20, and an interface 22. The memory 20 may be configured to store information accessible by the processor 18, including instructions executable by the processor 18 and/or data that may be retrieved, manipulated or stored by the processor 18. Further details associated with an exemplary controller 12 are disclosed in commonly owned U.S. patent application Ser. No. 15/710,323, which is incorporated by reference herein in the entirety.

Figure 3:
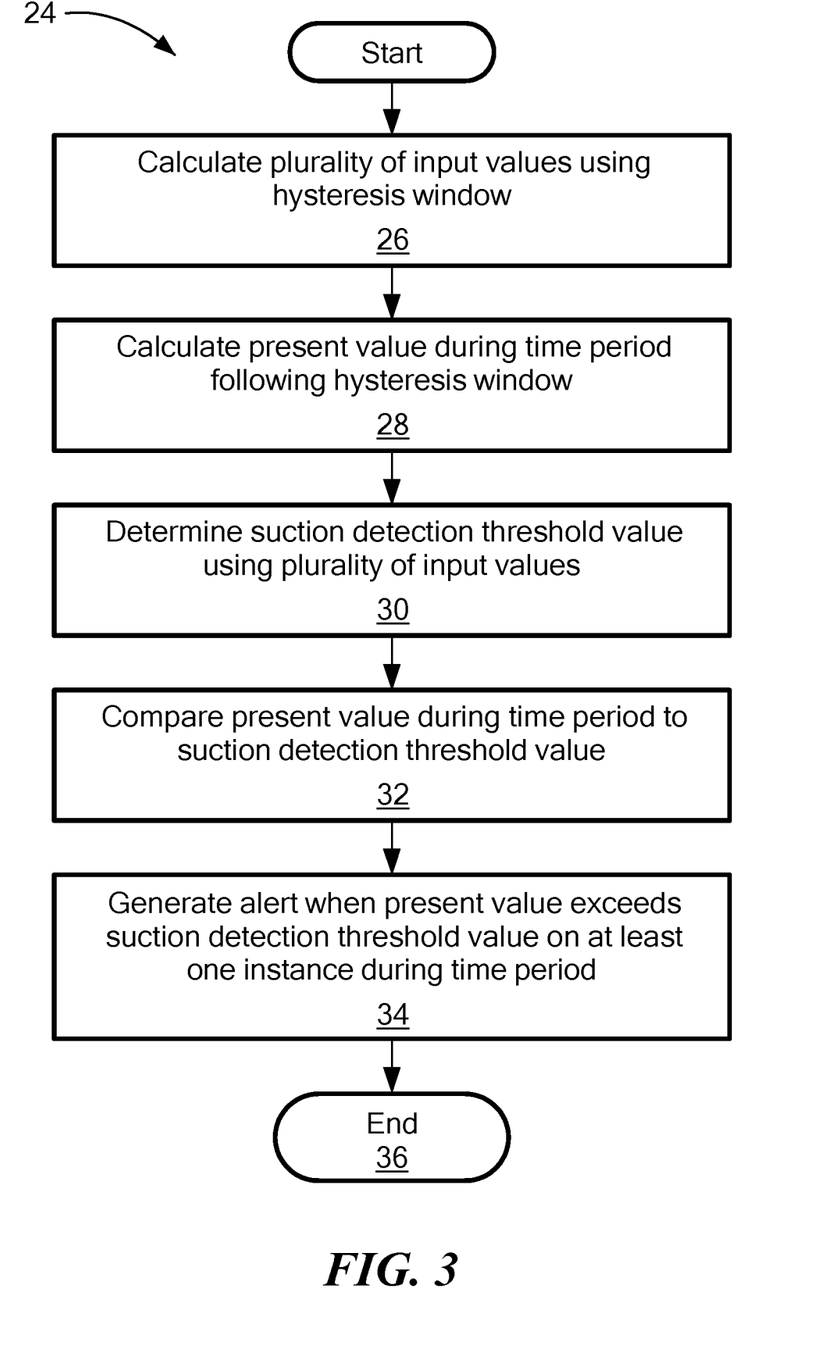
FIG. 3 is a flow chart depicting one more of the method steps of detecting the suction condition within the blood pump of FIG. 1.

FIG. 3 depicts a flowchart of a method 24, i.e., process, for detecting the suction condition within the blood pump 10 using one or more algorithms configured to provide an instantaneous detection of the suction condition, for example, at an onset of the condition or within one to two seconds of the onset. The method may include calculating one or more data values, such as a baseline value waveform and a pulsatility value waveform, relative to a hysteresis window and using the data values to calculate a suction detection threshold value. A present value may be calculated by dividing the pump speed by the pump current, independent of the flow within the blood pump, at a time that follows the hysteresis window. The suction condition is detected where the present value exceeds the suction detection threshold value on at least one instance.

The method 24 begins at task 26 in which the control circuit 14 calculates one or more of the data values based on the hysteresis window. Generally speaking, the hysteresis window or hysteresis represents a property of a system in which an output value incorporates a lag, delay, or history dependence, as opposed to being a strict function of a corresponding input, as is commonly understood by a person of ordinary skill in the art. The data values may be anticipated percentile values and/or a percentage of a minimum, a maximum, or a mean value from the hysteresis window calculated when the blood pump 10 is operating within a normal condition and not a suction condition. The normal condition generally includes a daily operating condition typical for the individual patient and blood pump 10 when no adverse conditions, such as the suction condition, are present within the blood pump 10.

Figure 4:
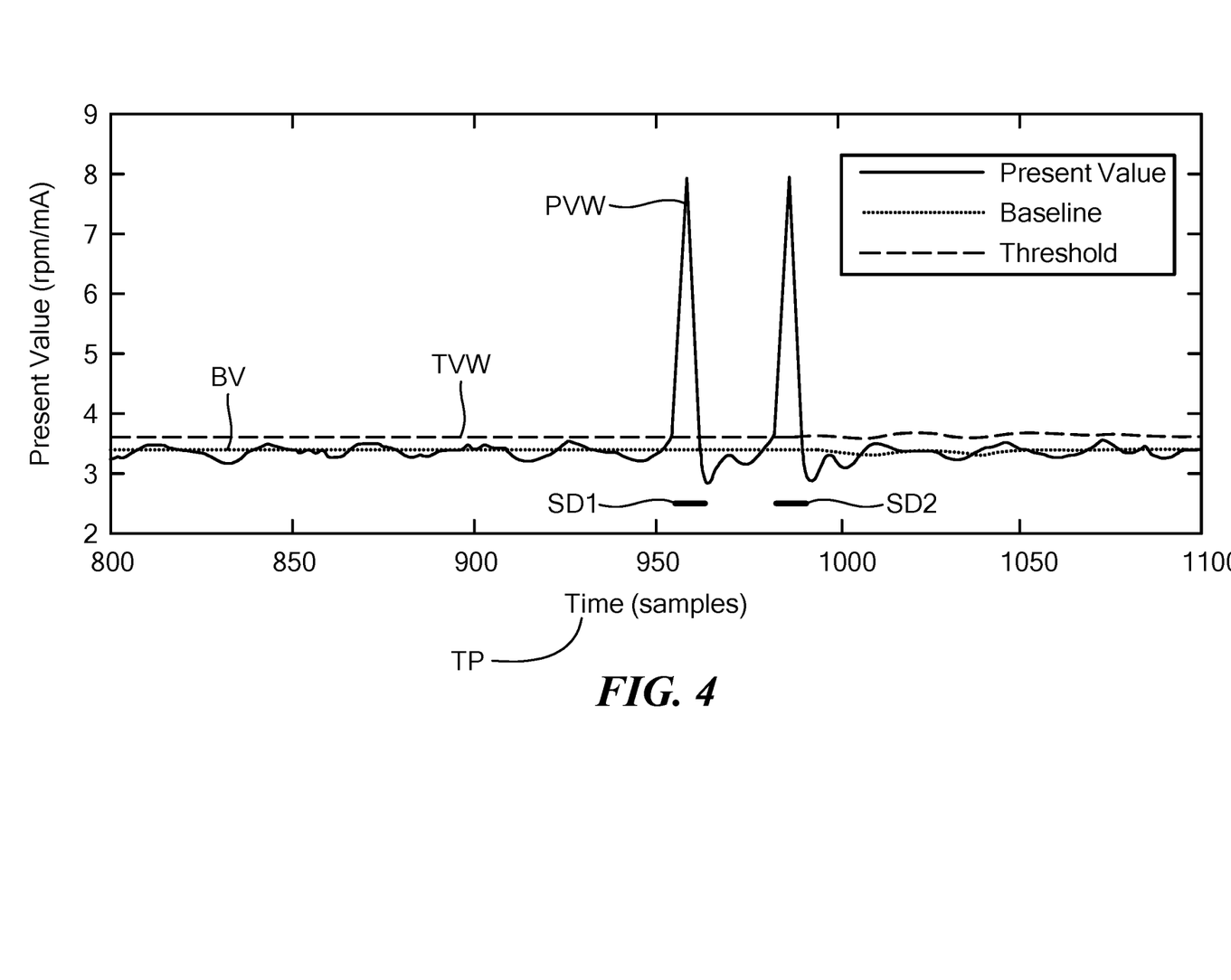
FIG. 4 is a graph depicting a suction condition shown using a baseline value waveform, a present value waveform, and a threshold value waveform over time in accordance with the method of FIG. 3.

With reference to FIG. 4, in one configuration, the control circuit 14 calculates the baseline value waveform "BV" that is within a 50th to 75th percentile of the hysteresis window and the pulsatility value waveform "PV" corresponding to a difference between an 70th to 90th percentile value and a 5th to 30th percentile value relative to the hysteresis window. FIG. 4 is provided for exemplary purposes as the time period, relative percentiles, and values described herein are utilized for illustrative purposes and may vary according to criteria input by a clinician or healthcare provider or the algorithms associated with the method.

At task 28, the control circuit 14 calculates the present value corresponding to the pump speed divided by the pump current during a time period, such as a select point or window of time, that may follow the hysteresis window. In other words, the present value is a time-based signal in the form of a single number, a range, and/or a waveform. The term present value and present value waveform may be used interchangeably herein. The pump speed and the pump current may be determined using various methods known in the art, such as and without limitation, a speed determination module and a current determination module, as discussed in commonly owned U.S. Pat. No. 9,511,179, referenced above and incorporated herein. With reference to FIG. 4, the present value is depicted using a present value waveform, generally designated as "PVW," plotted as rotations per minute ("RPM") over milliampere ("mA") relative to the time period, generally designated as "TP".

At task 30, the data values, i.e., the anticipated percentile values and/or percentages of the minimum, maximum, or mean values from the hysteresis window, are used within a suction detection equation to determine the suction detection threshold value "TV." In other words, a suction threshold is calculated using the data values. Referring to FIG. 4, the suction detection threshold value TV is shown in dashed dotted lines as a threshold value waveform "TVW" that may be compared to the present value to detect the suction condition during the time period "T". For example, the suction detection equation may include adding the baseline value waveform to the pulsatility value waveform with the pulsatility value waveform being multiplied by a multiplier "M." The equation may appear as: TV at T=BV+PV*M. In one configuration, the multiplier is between 0.5 to 2.0, such as 1.1; however, the multiplier may vary and may be a constant for numerous time periods.

At task 32, the control circuit 14 compares the present value to the suction detection threshold value. For example, FIG. 4 depicts the present waveform PW plotted relative to the threshold value waveform TVW. The suction condition is identified as present or detected when the present value is greater than the threshold value on at least one instance. FIG. 4 depicts two consecutive suction instances, labeled as "SD1" and "SD2," where the present waveform PVW exceeds the threshold value waveform TVW.

An alert may be generated at task 34 in response to the suction condition detection. The alert is not limited to being activated in response to the presence of the suction condition, but may be activated in response to one or more blood pump parameters or patient diagnostic metrics exceeding a designated threshold. The alert may be audible, visual, vibratory, or the like, and may be transmitted from a speaker of the blood pump 10 and/or the controller 12 to the patient or the clinician at a location remote from the blood pump 10.

Figure 5:
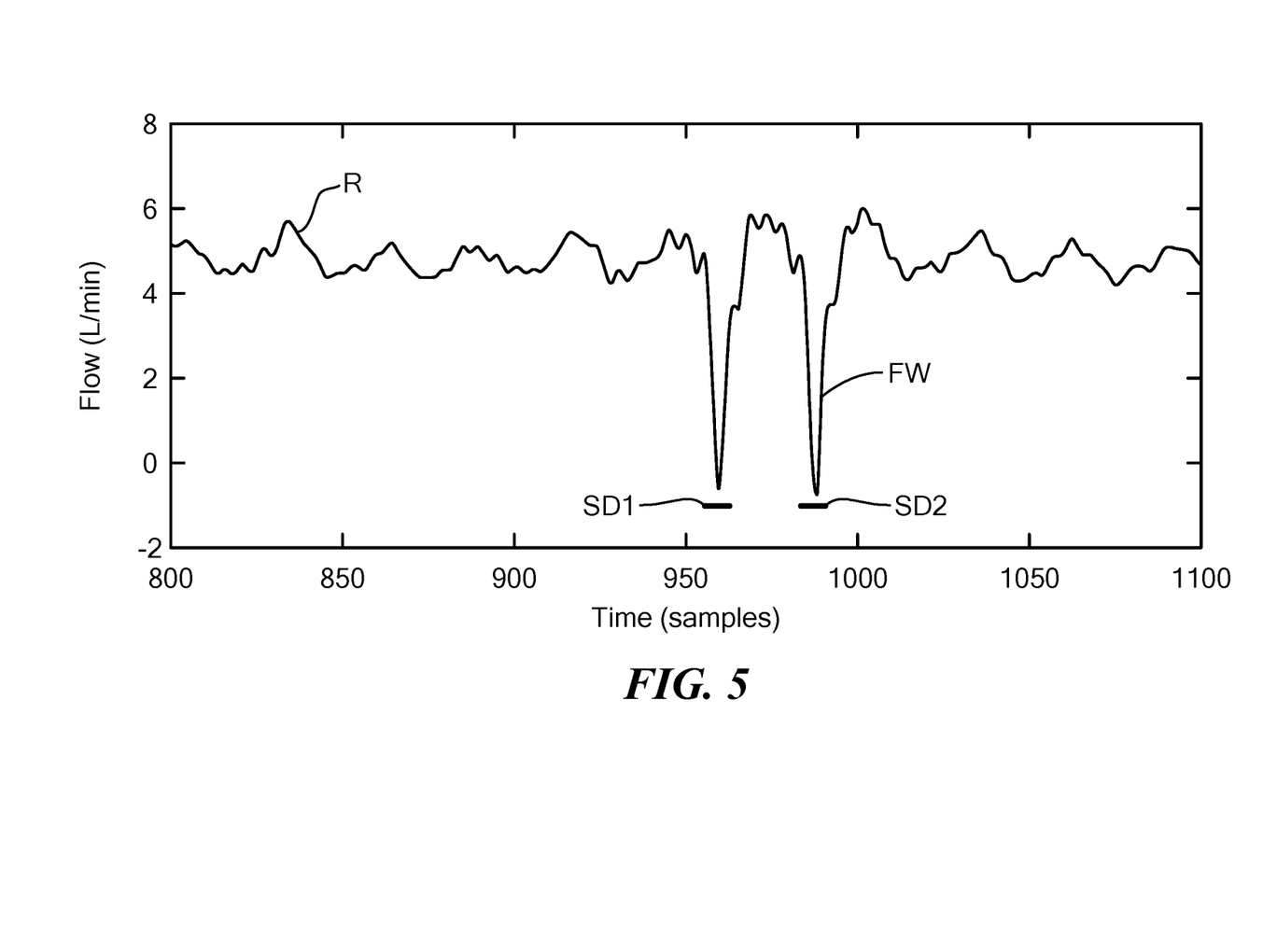
FIG. 5 is a graph depicting the suction condition of FIG. 4 shown using a flow waveform over time.
Figure 6:
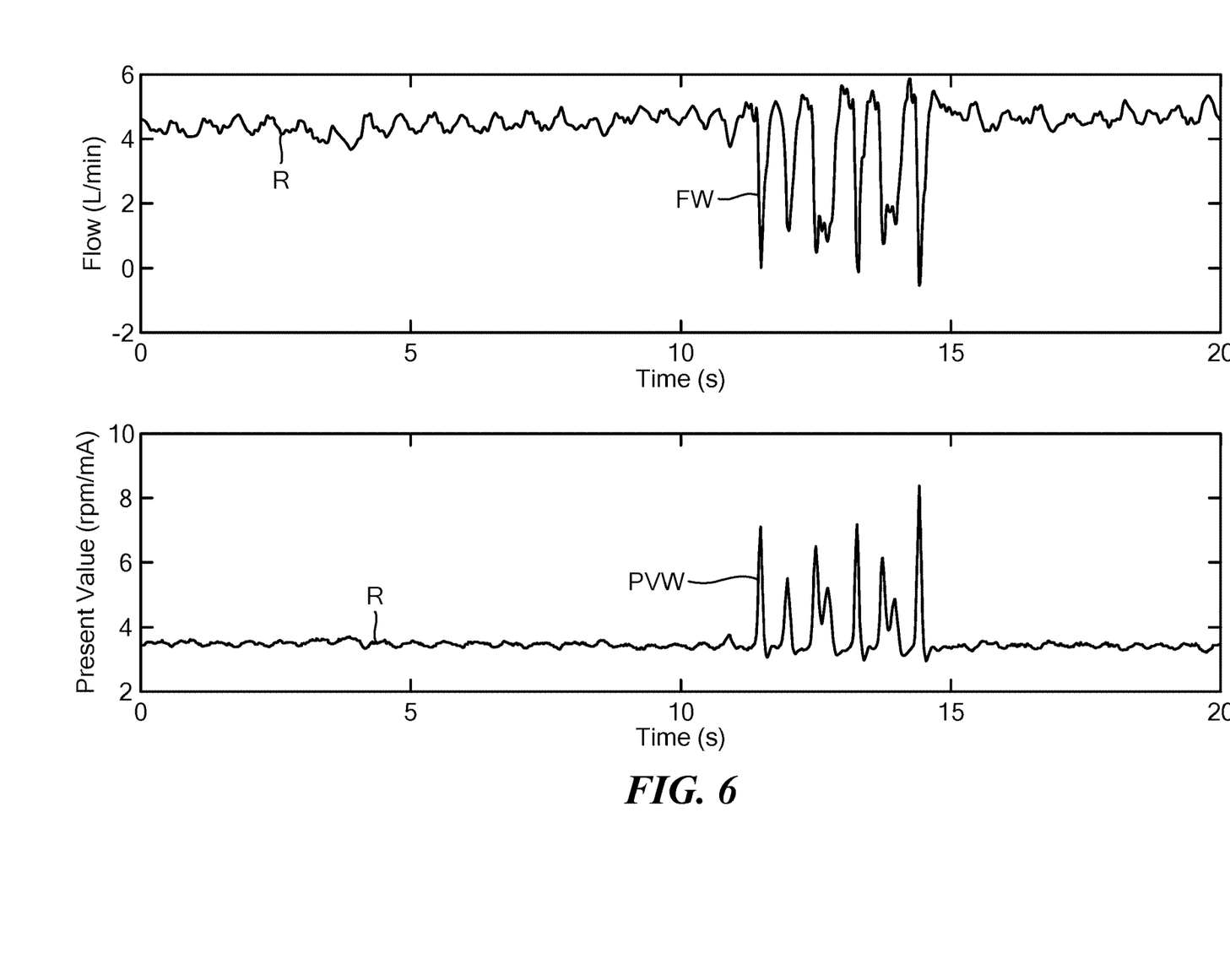
FIG. 6 is a graph depicting another instance of a suction condition shown using a flow waveform over time and a present value waveform over time.
Figure 7:
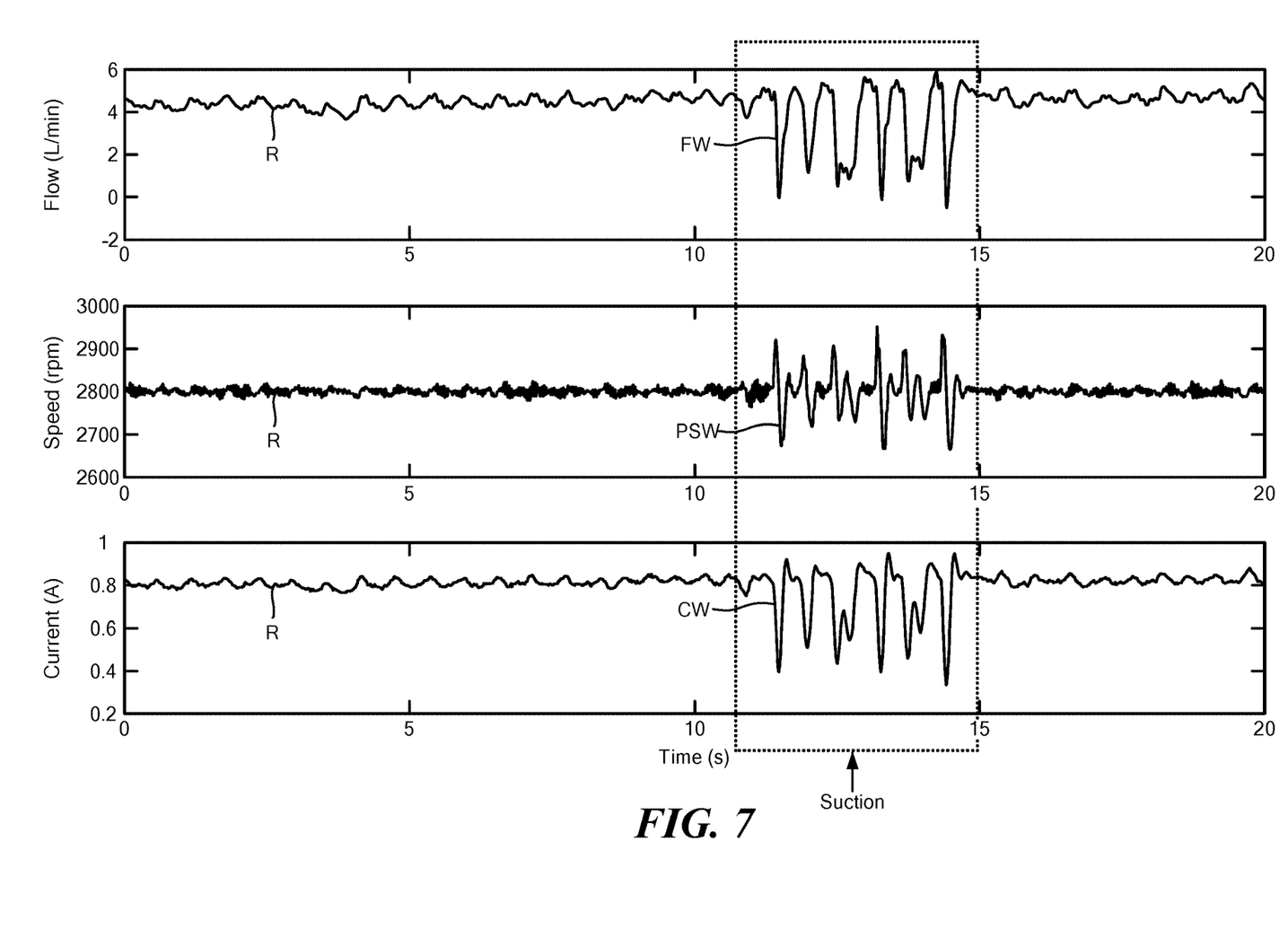
FIG. 7 is a graph depicting another instance of a suction condition shown using a flow waveform over time, a pump speed waveform over time, and a current waveform over time.

With reference to FIG. 5, a flow waveform "FW" is provided depicting the decrease in flow, i.e., blood flow, relative to a reference region "R" which occurs during the suction condition on the instances SD1 and SD2 when the present waveform PW exceeds the threshold value waveform TVW. FIGS. 6 and 7 depict similar graphs illustrating the decrease in flow and the corresponding increase in the present value which may be used to detect the suction condition. In particular, FIG. 6 depicts six consecutive decreases in the flow waveform FW occurring simultaneously with six consecutive increases in the present waveform PW which indicate the presence of the suction condition. FIG. 7 depicts six consecutive decreases in the flow waveform FW occurring simultaneously with six consecutive fluctuations in a pump speed waveform "PSW" and six consecutive decreases in a current waveform "CW" which indicate the presence of the suction condition.

Figure 8:
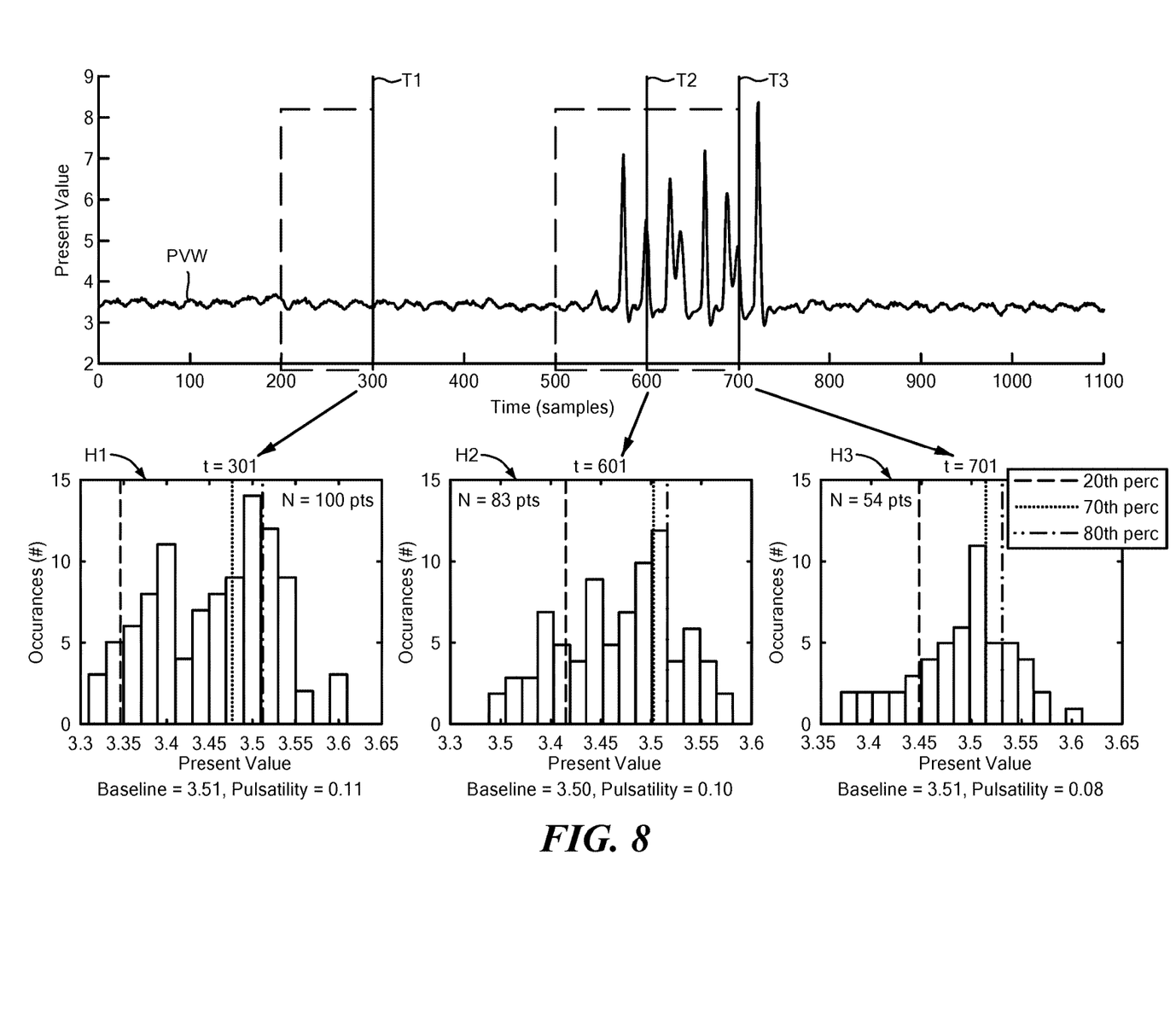
FIG. 8 is a graph depicting a present value waveform relative to time and three corresponding histograms.

Referring now to FIG. 8, as discussed above, the baseline value waveform and the pulsatility value waveform may be determined relative to the hysteresis window. For example, FIG. 8 depicts the present value waveform PVW including three data sections ending with designations T1, T2, and T3, containing data used to construct three corresponding histograms, designated as H1, H2, and H3, respectively. In particular, H1 depicts the baseline value waveform as 3.51, i.e., the 70th percentile of the present value. In addition, H1 depicts the pulsatility value waveform as 0.11, i.e., the 80th percentile minus the 20th percentile of the present value from one hundred non-suction time samples recorded. H2 depicts the baseline value waveform as 3.50 and the pulsatility value waveform as 0.10 from eighty-three non-suction time samples recorded, while H3 depicts the baseline value waveform as 3.51 and the pulsatility value waveform as 0.08 from fifty-four non-suction time samples recorded.

Figure 9:
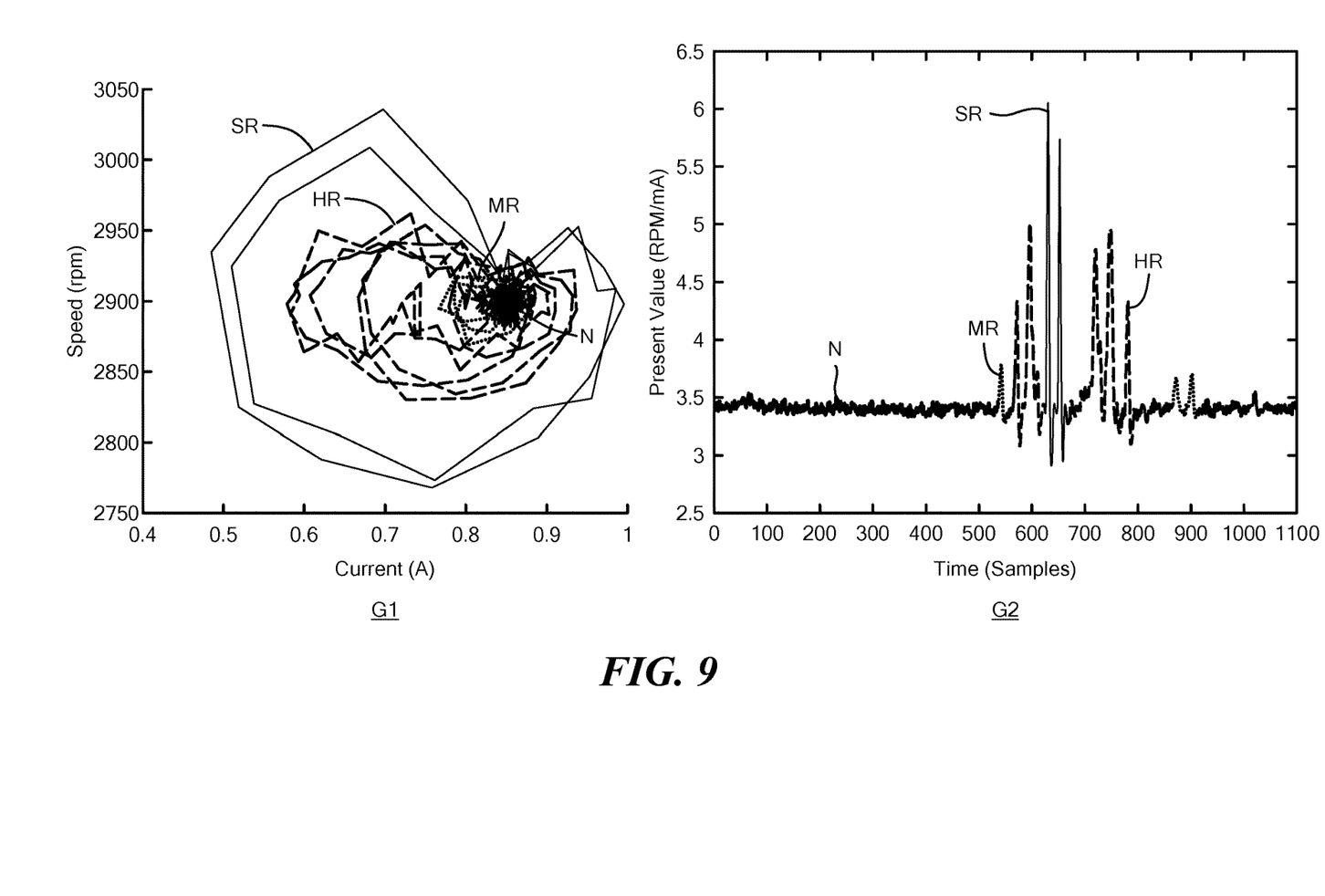
FIG. 9 is a first graph and a second graph depicting a severity classification of a suction condition.

With reference to FIG. 9, the control circuit 14 may be configured to classify a severity of the suction condition, such as by analyzing the pump speed relative to the pump current. During normal operation, the controller 12 is configured to maintain a relatively constant pump speed, taking into account adjustments to the current to accommodate pump speed changes associated with pressure changes and/or cardiac contraction. In the presence of the suction condition, the pump speed typically increases relative to the normal operative speed and the control circuit 14 is configured to reduce the current in an effort to return the pump speed to the normal operative speed. As such, greater fluctuations in the pump speed and the pump current may indicate suction conditions of greater severity. Such fluctuations in the pump speed may be graphically plotted relative to the pump current as a loop, with the severity of the suction condition increasing in accordance with an increase in an area of the loop.

For example, FIG. 9 includes a first graph "G1" depicting the loop having one or more severity regions, such as a severe region "SR" in solid lines forming a widest region of the loop and a hazardous region "HR" in dashed lines within the severe region. A mildly severe region "MW" is depicted in dotted lines having a width less than a width of the severe or hazardous region and a normal region "N" is depicted in solid lines having a relatively narrow width within the severe region. The same severity regions are shown in a second graph "G2" plotted as a function of the pump flow over time. The parameters used to classify each severity region may be predetermined by the user, such as a clinician, or may be developed by one or more algorithms associated with the method. The graphs in FIG. 9 are provided for illustrative purposes and are not intended to be limiting as other classifications may be used to identify the severity of the suction condition.

Figure 10:
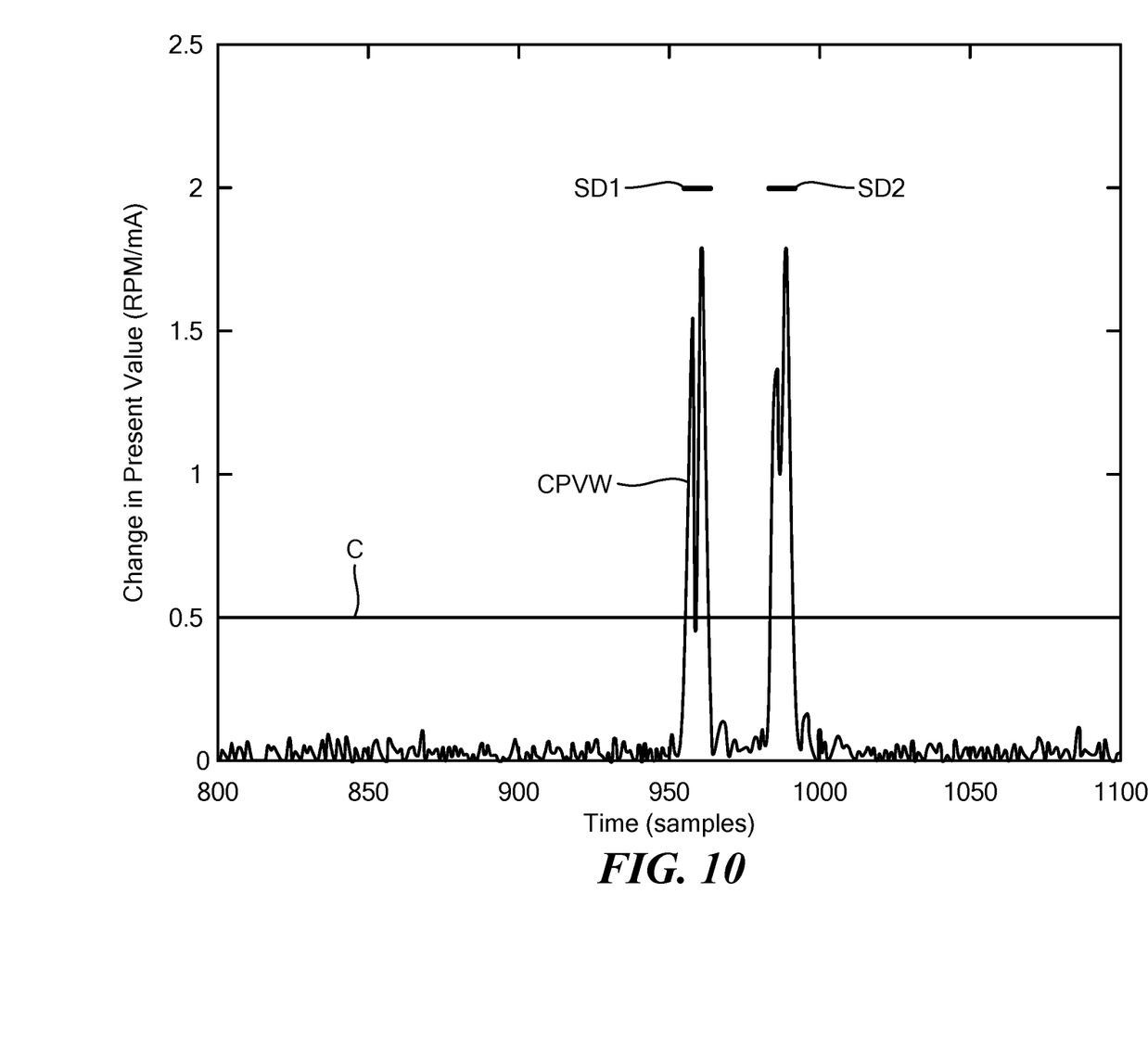
FIG. 10 is a graph depicting a change in a present value waveform relative to time.

Referring now to FIG. 10, an adverse event, such as the suction condition, may be detected using an alternative method and algorithm different than method 24 described above. The alternative method and algorithm includes using a difference in the present value at two or more different points. Such difference may be analogous to taking a slope of two consecutive present value points. For example, in one configuration, at a select time "t" a change in the present value may be expressed as a change in present value ("CPV") at time t=present value at time t−present value at time (t−1). Such equation may also be written as CPV=PV (t)−PV (t−1), where PV=speed/current.

FIG. 10 depicts the data provided in FIGS. 4 and 5 and includes a derived waveform called a "change in present value waveform," designated "CPVW". The suction condition is indicated when a change in the present value waveform CPVW is greater than a designated constant "C," which may be designated as the threshold. In other words, the CPVW exceeding the threshold indicates that suction is detected. FIG. 10 depicts the designated constant as exemplary value 0.5, however, other values may be used to perform the method and algorithm. In response to the suction condition being detected, the method may include adjusting at least one pump parameter, such as the speed, current, etc., of the blood pump 10 using the controller 12. The adjustments may be made in attempt to resolve the adverse event. In addition to adjusting the blood pump 10, one or more alarms may be activated in response to the detected suction condition or other condition, as discussed above.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for detecting a suction condition in an implantable blood pump, the system comprising:
   a controller in communication with the blood pump, the controller including a control circuit configured to:
   calculate a plurality of data values using a hysteresis window;
   calculate a present value during a time period, the present value corresponding to a pump speed divided by a pump current following the hysteresis window;

determine a suction detection threshold value using the plurality of data values;

compare the present value during the time period to the suction detection threshold value;

classify a severity of a detected suction condition based on a loop having one or more severity regions based on the determined suction detection threshold, a narrower width compared to a wider width of the one or more severity regions is indicative of a less severe suction condition; and generate an alert when the present value exceeds the suction detection threshold value on a plurality of consecutive instances during the time period, the alert corresponding to a suction condition.

2. The system of claim 1, wherein the time period is a one to five second hysteresis window.

3. The system of claim 1, wherein the plurality of data values includes a baseline value waveform between a 50th to 75th percentile relative to the hysteresis window.

4. The system of claim 3, wherein the baseline value waveform is an adaptive value.

5. The system of claim 1, wherein the plurality of data values includes a first pulsatility percentile value between a 5th to 30th percentile relative to the hysteresis window and a second pulsatility percentile value between a 70th to 95th percentile value relative to the hysteresis window.

6. The system of claim 5, wherein the control circuit is configured to calculate a pulsatility value waveform corresponding to a difference between the first pulsatility percentile value and the second pulsatility percentile value.

7. The system of claim 6, wherein the control circuit is configured to determine the suction detection threshold value using a suction detection equation, the suction detection equation including adding a baseline value waveform to the pulsatility value waveform, the pulsatility value waveform being multiplied by a multiplier.

8. The system of claim 7, wherein the multiplier is a constant over a plurality of time periods.

* * * * *